United States Patent
Galaffu et al.

(10) Patent No.: US 10,617,140 B2
(45) Date of Patent: Apr. 14, 2020

(54) IRON-FORTIFIED FOOD COMPOSITION

(71) Applicant: NESTEC S.A., Vevey (CH)

(72) Inventors: Nicola Galaffu, Ornex (FR); Edwin Alberto Habeych Narvaez, Lausanne (CH); Sylvie Joelle Merinat, Moudon (CH); Brigitte Rey, Bulle (CH)

(73) Assignee: Societe des Produits Nestle S.A., Vevey (CH)

( * ) Notice: Subject to any disclaimer, the term of this patent is extended or adjusted under 35 U.S.C. 154(b) by 217 days.

(21) Appl. No.: 15/756,776

(22) PCT Filed: Sep. 1, 2016

(86) PCT No.: PCT/EP2016/070659
§ 371 (c)(1),
(2) Date: Mar. 1, 2018

(87) PCT Pub. No.: WO2017/037200
PCT Pub. Date: Mar. 9, 2017

(65) Prior Publication Data
US 2018/0249752 A1    Sep. 6, 2018

(30) Foreign Application Priority Data

Sep. 3, 2015 (EP) .................................. 15183695

(51) Int. Cl.
| | | |
|---|---|---|
| A23L 33/165 | (2016.01) |
| A23L 2/52 | (2006.01) |
| A23L 33/175 | (2016.01) |
| A61K 31/6615 | (2006.01) |
| A61K 33/26 | (2006.01) |
| A23C 9/13 | (2006.01) |
| A61K 33/02 | (2006.01) |
| A23C 9/152 | (2006.01) |
| A23L 29/00 | (2016.01) |
| A23L 33/105 | (2016.01) |
| A23L 23/10 | (2016.01) |

(52) U.S. Cl.
CPC .......... *A23L 33/165* (2016.08); *A23C 9/1322* (2013.01); *A23C 9/1522* (2013.01); *A23L 2/52* (2013.01); *A23L 29/05* (2016.08); *A23L 33/105* (2016.08); *A23L 33/175* (2016.08); *A61K 31/6615* (2013.01); *A61K 33/02* (2013.01); *A61K 33/26* (2013.01); *A23L 23/10* (2016.08); *A23V 2002/00* (2013.01); *A23V 2200/30* (2013.01); *A23V 2250/1592* (2013.01); *A23V 2250/2134* (2013.01)

(58) Field of Classification Search
CPC .... A23L 33/165; A23L 33/175; A23L 33/105; A23L 29/05
USPC ........................................... 426/74, 590, 656
See application file for complete search history.

(56) References Cited

U.S. PATENT DOCUMENTS

2009/0035385 A1    2/2009  Bortz

FOREIGN PATENT DOCUMENTS

| WO | 0167897 | 9/2001 |
| WO | 2013092336 | 6/2013 |

OTHER PUBLICATIONS

Graf et al. "Effects of Phytate on Mineral Bioavailability in Mice" The Journal of Nutrition, 1984, vol. 114, pp. 1192-1198, XP009159152.

*Primary Examiner* — Helen F Heggestad
(74) *Attorney, Agent, or Firm* — K&L Gates LLP

(57) ABSTRACT

A composition for fortifying food and/or beverages comprising a complex of Fe(III), phytic acid and an amino compound selected from the group consisting of ammonium hydroxide; ammonium carbonate; ammonium phosphate dibasic; ammonium sodium phosphate dibasic and triammonium phosphate.

9 Claims, 1 Drawing Sheet

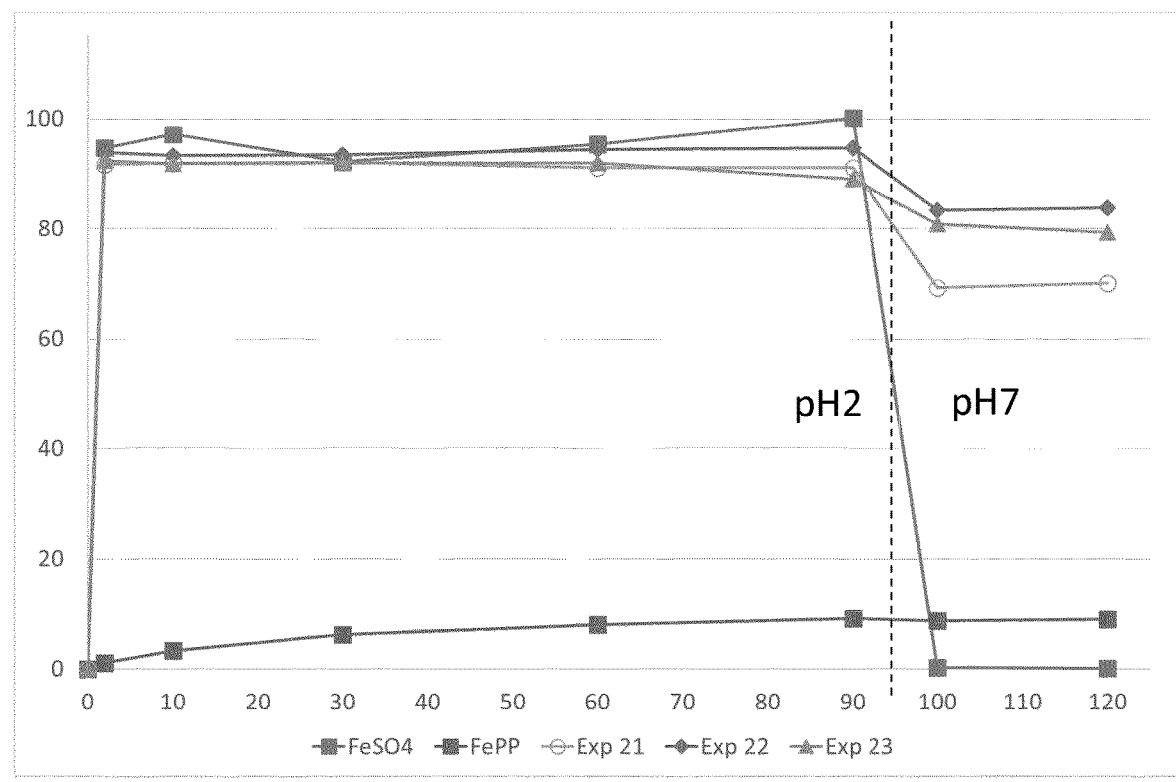

US 10,617,140 B2

IRON-FORTIFIED FOOD COMPOSITION

CROSS REFERENCE TO RELATED APPLICATIONS

The present application is a National Stage of International Application No. PCT/EP2016/070659, filed on Sep. 1, 2016, which claims priority to European Patent Application No. 15183695.4, filed on Sep. 3, 2015, the entire contents of which are being incorporated herein by reference.

FIELD OF THE INVENTION

The present invention relates to compositions for fortifying food and/or beverages with iron. More specifically, the present invention relates to compositions comprising Fe(III), phytic acid and an amino compound, which provide stable and soluble sources of iron for fortifying food and/or beverages.

BACKGROUND TO THE INVENTION

Nutritional mineral deficiencies (also referred to as micronutrient malnutrition) affect a large proportion of the human population and are particularly widespread in developing countries. Deficiency in iron is especially common, affecting more than two billion people world-wide, and is the only nutrient deficiency that is significantly prevalent in industrialised countries. Iron deficiency is associated with a range of health problems, including impairment of work performance, increased maternal and child mortality, and poor cognitive development in children.

Iron deficiencies originate when physiological requirements are not met by mineral absorption from the diet, for example due to low iron bioavailability. Dietary iron bioavailability may be low, for example, in populations having monotonous plant-based diets with little meat. Indeed, a major cause of low iron bioavailability is related to the presence of anti-nutritional factors that are naturally present in cereals and legumes. These factors form insoluble complexes with iron and interfere with its absorption.

Fortifying food with iron is a well known approach to increase dietary iron intake, but can pose a number of difficulties. A significant problem is caused by the general incompatibility between bioavailability and stability of iron compounds. Typically, the most bioavailable iron compounds are the most reactive within the food matrix. As such, fortifying foods with iron can lead to a number of undesirable changes in properties of the food, in particular organoleptic properties of the food. For example iron can accelerate oxidation reactions, adversely altering a food's flavour, and iron can also form complexes with phenolic chromophore compounds, leading to unwanted colour changes in the food.

For example, ferrous (i.e. Fe(II)) sulfate, which is a reference iron compound for food fortification in humans, causes sensory changes in the food vehicle in the presence of polyphenols or high amounts of lipids. In contrast, more stable iron sources, which are typically water-insoluble (e.g. ferric (i.e. Fe(III)) pyrophosphate), have relatively low bioavailability compared to water-soluble compounds.

A number of approaches have been taken during attempts to improve iron fortification of foods. Encapsulated ferrous sulfate has been considered, because it could provide a highly bioavailable iron source while maintaining stability through encapsulation of the formulation. However, bioavailability is highly dependent on the coating used and in many cases bioavailability of the coated iron source is reduced. Encapsulation also increases production costs. Moreover, most coatings used for encapsulation, which are lipid based, give rise to problems associated with melting during the different heat treatment stages of the manufacture of many food products.

Alternative approaches have used iron-containing nanoparticles that have been stabilised with biopolymers (EP 1743530), or ferric EDTA (ethylenediaminetetraacetic acid), which has good bioavailability and stability (U.S. Ser. No. 10/969,434; published as US 2005/0053696), for iron fortification. However, the use of nanotechnology and EDTA in food products is meeting with increased consumer resistance. Furthermore, sodium iron EDTA is expensive and not stable in all food matrices (e.g. chicken bouillon).

Accordingly, there remains a significant need for compositions and methods that enable fortification of foods and beverages with iron. In particular, there remains a need for compositions and methods that provide a soluble, preferably bioavailable source of iron that has minimal effect on the organoleptic properties of foods.

SUMMARY OF THE INVENTION

The present inventors have surprisingly found that water-soluble complexes of Fe(III) can be prepared using phytic acid in the presence of amino compounds. Although water-soluble Fe(II):phytic acid complexes are known, complexes of Fe(III) with phytic acid were previously regarded as highly insoluble. Indeed, the use of phytic acid in food products has previously been avoided due to its potential for binding multivalent cations. The resulting complexes are usually insoluble under physiological conditions, with the result that digestion by humans is difficult. Consequently, phytic acid has traditionally been considered anti-nutritional.

Moreover, the present inventors have found that the compositions of the present invention can be used to fortify food and beverages with little effect on their organoleptic properties. In particular, the present inventors have found that fruit or vegetable-containing foods and bouillon, which were previously regarded as difficult to fortify with iron, may be fortified with the compositions of the present invention with minimal effect on their colour. While not wishing to be bound by theory, this may be due to Fe(III) exhibiting greater stability than the soluble Fe(II) compositions that are commonly used (e.g. ferrous sulfate).

Accordingly, in one aspect the present invention provides a composition for fortifying food and/or beverages comprising a complex of Fe(III), phytic acid and an amino compound selected from the group consisting of ammonium hydroxide; ammonium carbonate; ammonium phosphate dibasic; ammonium sodium phosphate dibasic and triammonium phosphate. The present invention also provides a composition for fortifying food and/or beverages comprising a complex of Fe(III), phytic acid and an amino compound, wherein the composition does not comprise a carboxylic acid-containing compound other than an optional amino acid.

In another aspect, the present invention provides a composition for fortifying food and/or beverages comprising Fe(III), phytic acid and an amino compound selected from the group consisting of ammonium hydroxide; ammonium carbonate; ammonium phosphate dibasic; ammonium sodium phosphate dibasic and triammonium phosphate. The present invention also provides a composition for fortifying food and/or beverages comprising Fe(III), phytic acid and an amino compound, wherein the composition does not comprise a carboxylic acid-containing compound other than an optional amino acid.

The composition of the invention may comprise Fe(III) ions of which some or all are in the form of a water-soluble complex with some or all of the phytic acid.

In one embodiment, the amino compound is selected from the group consisting of ammonium hydroxide; ammonium carbonate; ammonium phosphate dibasic; ammonium sodium phosphate dibasic and triammonium phosphate.

In a preferred embodiment, the amino compound is ammonium hydroxide

In another embodiment, the composition further comprises an amino acid. The amino acid that is comprised in the composition may be comprised in the complex of Fe(III), phytic acid and the amino compound. In one embodiment, the amino acid that is comprised in the composition is selected from histidine, arginine, lysine, glycine, aspartic acid, glutamic acid, glutamine and proline, or a combination thereof. In another embodiment, the amino acid that is comprised in the composition is glycine. Preferably, the amino acid that is comprised in the composition is histidine. The combination of amino acids comprised in the composition may be histidine and lysine. The combination of amino acids comprised in the composition may be histidine and arginine. The combination of amino acids comprised in the composition may be histidine and glycine. The combination of amino acids comprised in the composition may be histidine and glutamine.

The water-soluble compositions of the invention include compositions that are almost entirely soluble in aqueous solution, i.e. dissolve to an extent that a solution retaining a haze is produced. In one embodiment, at least 70%, 75%, 80%, 85%, 90%, 91%, 92%, 93%, 94%, 95%, 96%, 97%, 98% or 99% by weight of the composition dissolves in aqueous solution. Preferably, the composition dissolves completely in aqueous solution.

The molar ratios of the components of the composition may be any ratios that provide a water-soluble composition.

In one embodiment, the molar ratio of Fe(III) to phytic acid is about 0.1:1 to about 4:1. In another embodiment, the molar ratio of Fe(III) to phytic acid is about 0.1:1 to about 2.5:1. In another embodiment, the molar ratio of Fe(III) to phytic acid is about 0.5:1 to about 2.4:1. In another embodiment, the molar ratio of Fe(III) to phytic acid is about 1:1 to about 2:1. In another embodiment, the molar ratio of Fe(III) to phytic acid is about 1.2:1 to about 1.6:1. Preferably, the molar ratio of Fe(III) to phytic acid is about 2:1.

In one embodiment, the molar ratio of the amino compound to phytic acid is about 0.5:1 to about 20:1. In another embodiment, the molar ratio of the amino compound to phytic acid is about 1:1 to about 20:1. In another embodiment, the molar ratio of the amino compound to phytic acid is about 2:1 to about 20:1. In another embodiment, the molar ratio of the amino compound to phytic acid is about 2:1 to about 15:1. In another embodiment, the molar ratio of the amino compound to phytic acid is about 2:1 to about 10:1. In another embodiment, the molar ratio of the amino compound to phytic acid is about 2:1 to about 3.5:1.

In one embodiment, the molar ratio of the amino compound to Fe(III) is about 4:1 to about 30:1. In another embodiment, the molar ratio of the amino compound to Fe(III) is about 4.4:1 to about 15:1. In another embodiment, the molar ratio of the amino compound to Fe(III) is about 4.4:1 to about 10:1. In another embodiment, the molar ratio of the amino compound to Fe(III) is about 4.4:1 to about 7.5:1.

In one embodiment, the molar ratio of the amino acid to phytic acid is about 0.1:1 to about 15:1. In another embodiment, the molar ratio of the amino acid to phytic acid is about 0.1:1 to about 10:1. In another embodiment, the molar ratio of the amino acid to phytic acid is about 0.5:1 to about 10:1. In another embodiment, the molar ratio of the amino acid to phytic acid is about 1:1 to about 10:1. In another embodiment, the molar ratio of the amino acid to phytic acid is about 4:1 to about 10:1. In another embodiment, the molar ratio of the amino acid to phytic acid is about 1:1 to about 5:1.

In one embodiment, the molar ratio of the total of the amino compound plus amino acid to phytic acid is greater than about 4.5:1. In another embodiment, the molar ratio of the total of the amino compound plus amino acid to phytic acid is about 4.5:1 to about 25:1. In another embodiment, the molar ratio of the total of the amino compound plus amino acid to phytic acid is about 4.5:1 to about 20:1, for example about 4.5:1 to about 15:1 or about 4.5:1 to about 10:1. In another embodiment, the molar ratio of the total of the amino compound plus amino acid to phytic acid is about 5.5:1 to about 25:1, for example about 5.5:1 to about 20:1, about 5.5:1 to about 15:1, about 5.5:1 to about 10:1, about 7:1 to about 25:1, about 7:1 to about 20:1, about 7:1 to about 15:1 or about 7:1 to about 10:1.

In one embodiment, the molar ratio of the total of the amino compound plus amino acid to Fe(III) is about 4.5:1 to about 25:1. In another embodiment, the molar ratio of the total of the amino compound plus amino acid to Fe(III) is about 4.5:1 to about 15:1. In another embodiment, the molar ratio of the total of the amino compound plus amino acid to Fe(III) is about 4.5:1 to about 10:1. In another embodiment, the molar ratio of the total of the amino compound plus amino acid to Fe(III) is about 4.5:1 to about 7.5:1.

In one embodiment the molar ratio of phytic acid to Fe(III) may be 1 to between 0.5 and 2, and the molar ratio of phytic acid to to amino acid may be 1 to between 0.5 and 2.5. In a further embodiment the composition may comprise glycine and histidine as amino acids; the molar ratio of phytic acid to Fe(III) being 1 to between 1.5 and 2, the molar ratio of phytic acid to glycine being 1 to between 1.5 and 2.5 glycine, the molar ratio of phytic acid to histidine being 1 to between 0.3 and 1, and the amino compound being ammonium hydroxide added in an amount to adjust the pH to between 5.5 and 6.0. Such compositions are effective at fortifying food and/or beverages without excessive ingredient cost.

In one embodiment, the composition is in the form of an aqueous solution or a water-soluble solid. The composition in the form of an aqueous solution may comprise high concentrations of the complex and remain stable. For example the composition in the form of an aqueous solution may comprise at least 10 wt. % complex in solution, for example at least 20 wt. % complex in solution, for example at least 30 wt. % complex in solution, The aqueous solution composition may be in the form of a concentrated stock solution for addition to food and/or beverage products, such as water (e.g. bottled water).

The solid composition may be in the form of a powder or granules. A powder composition may be contained in a sachet. A powder composition according to the present invention may be used to sprinkle onto a food or beverage. In one embodiment, the composition is in the form of a sachet containing a powder, wherein the powder can be dispersed into a beverage (e.g. water, fruit juice or milk) to provide a palatable nutrient liquid for oral administration.

In another aspect, the present invention provides a composition for fortifying food and/or beverages, wherein the composition is prepared by (for example is obtainable by) mixing an Fe(III) compound, phytic acid and an amino compound selected from the group consisting of ammonium hydroxide; ammonium carbonate; ammonium phosphate dibasic; ammonium sodium phosphate dibasic and triammonium phosphate. The present invention also provides a composition for fortifying food and/or beverages, wherein the composition is prepared by (for example is obtainable by) mixing an Fe(III) compound, phytic acid and an amino compound, wherein the composition does not comprise a carboxylic acid-containing compound other than an optional amino acid. The present invention also provides a composition for fortifying food and/or beverages, wherein the composition is prepared by (for example is obtainable by) mixing an Fe(III) compound, phytic acid and an amino compound in the absence of a carboxylic acid-containing compound other than an optional amino acid. The features of the composition may be as described herein for the compositions and methods of the invention.

In another aspect, the present invention provides the use of the composition of the invention for fortifying a food or beverage product with iron.

In one embodiment, the use of the compositions of the invention reduces the effect of iron fortification on the organoleptic properties of the food or beverage (e.g. in comparison to other iron compositions, such as ferrous sulfate or ferric pyrophosphate). For example, the use of the compositions of the invention may improve the stability of the colour of the food or beverage fortified with iron (e.g. reduce the change in colour of the food or beverage as a result of iron fortification with the compositions of the invention in comparison with other iron compositions, such as ferrous sulfate or ferric pyrophosphate).

A colour change may be considered to be a difference in colour of sufficient magnitude that a human observer would perceive the difference between two samples shown one after the other but not simultaneously. For example, a colour change may be considered to be a CIELAB $\Delta Eab^*$ colour difference greater than 2, for example greater than 3. In one embodiment, the compositions of the invention cause a CIELAB $\Delta Eab^*$ colour difference of less than 7, for example less than 6.5, 5, 4.5, 4, 3.5, 3, 2.5, 2 or 1.5, when used to fortify a food or beverage product, such as a product described herein.

In another embodiment, the use of the compositions of the invention increases the bioavailability of iron, in particular Fe(III), in a food or beverage, for example in comparison with other iron compositions, such as ferric pyrophosphate.

In another aspect, the present invention provides a food or beverage product which has been fortified with the composition of the present invention, for example a food or beverage product obtainable by fortification with the composition of the present invention.

In one embodiment, the food or beverage product is a yoghurt, bouillon, water (e.g. bottled water), seasoning, sauce, milk powder, milk drink, milk-based dessert, pet food, cereal, pasta, noodle or baby food product. Preferably, the food or beverage product is a yoghurt, bouillon or water (e.g. bottled water).

In another aspect, the present invention provides a method of preparing a water-soluble composition, wherein the method comprises the steps:

(a) mixing in an aqueous solution a source of Fe(III), phytic acid, an amino compound and optionally an amino acid; and (b) optionally heating the mixture, preferably to at least 50° C., wherein the amino compound is selected from the group consisting of ammonium hydroxide; ammonium carbonate; ammonium phosphate dibasic; ammonium sodium phosphate dibasic and triammonium phosphate. The present invention also provides a method of preparing a water-soluble composition, wherein the method comprises the steps:

(a) mixing in an aqueous solution a source of Fe(III), phytic acid, an amino compound and optionally an amino acid; and (b) optionally heating the mixture, wherein the composition does not comprise a carboxylic acid-containing compound other than an optional amino acid.

In one embodiment, the method further comprises the step of removing the water from the product obtained from step (a) or (b) to provide a solid composition. The water may be removed by any standard drying technique, such as freeze drying or spray drying. Preferably, the water is removed by freeze drying.

In one embodiment, the amino compound is selected from the group consisting of ammonium hydroxide; ammonium carbonate; ammonium phosphate dibasic; ammonium sodium phosphate dibasic and triammonium phosphate.

In a preferred embodiment, the amino compound is ammonium hydroxide. In one embodiment, the amino acid optionally added in step (a) is selected from histidine, arginine, lysine, glycine, aspartic acid, glutamic acid, glutamine and proline, or a combination thereof. In another embodiment, the amino acid optionally added in step (a) is selected from histidine, arginine, lysine, glycine, or a combination thereof. In another embodiment, the amino acid optionally added in step (a) is glycine. Preferably, the amino acid optionally added in step (a) is histidine.

In one embodiment, the source of Fe(III) is selected from the group consisting of Fe(III) sulfate, Fe(III) citrate, Fe(III) choline citrate, Fe(III) ammonium citrate and Fe(III) chloride. Preferably, the source of Fe(III) is Fe(III) sulfate.

In one embodiment, step (b) of the method comprises heating the mixture to at least 60° C. In another embodiment, step (b) of the method comprises heating the mixture to at least 70° C. In another embodiment, step (b) of the method comprises heating the mixture to at least 80° C.

The molar ratios of the individual components mixed in step (a) may be as described herein for the compositions of the invention.

In another aspect, the present invention provides a method of fortifying a food or beverage product comprising adding the composition of the invention to the food or beverage product.

In another aspect, the present invention provides a composition of the invention for use in treating Iron Deficiency Anaemia (IDA).

BRIEF DESCRIPTION OF THE DRAWINGS

FIG. 1 is a plot of percentage relative bioaccessibility against time in minutes, as described in Example 10; FeSa$_4$ ■, Fe pyrophosphate ●, Exp 21 O, Exp 22 ◆ and Exp 23 ▲.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J.O'D. (1990) In Situ Hybridization: Principles and Practice, Oxford University Press; Gait, M. J. (1984) Oligonucleotide Synthesis: A Practical Approach, IRL Press; Lilley, D. M. and Dahlberg, J. E. (1992) Methods in Enzymology: DNA Structures Part A: Synthesis and Physical Analysis of DNA, Academic Press; Damodaran, S., Parkin, K. L., Fennema, O. R. (2007) Fennema's Food Chemistry, 4th Edition, CRC Press; Gispert, J. R. (2008) Coordination Chemistry, Wiley-VCH; Crichton, R. (2001) Inorganic Biochemistry of Iron Metabolism, 2nd Edition, Wiley; and Kaim, W., Schwederski, B., Klein, A. (2013) Bioinorganic Chemistry: Inorganic Elements in the Chemistry of Life, 2nd Edition, Wiley. Each of these general texts is herein incorporated by reference.

In one aspect the present invention provides a composition for fortifying food and/or beverages comprising a complex of Fe(III), phytic acid and an amino compound selected from the group consisting of ammonium hydroxide; ammonium carbonate; ammonium phosphate dibasic; ammonium sodium phosphate dibasic and triammonium phosphate.

The compositions of the invention may be any compositions that are suitable for ingestion by animals, preferably humans. The compositions may be ingested directly, however preferably the compositions of the invention are for use in fortifying foods and/or beverages with iron, i.e. increasing the amount of bioavailable iron in the food or beverage.

The food or beverage products to which the composition of the invention can be added include any product capable of being fortified with iron. Example food or beverage products include yoghurt, bouillon, water (e.g. bottled water), seasoning, sauce, milk powder, milk drink, milk-based dessert, pet food, cereal, pasta, noodle or baby food products.

The dietary reference intake (DRI) for iron typically varies from 8 mg iron/person/day for adult men to 18 mg iron/person/day for menstruating women. The DRI is far greater for pregnant women, i.e. 27 mg iron/person/day. For breast-feeding mothers, the DRI is 9-10 mg iron/person/day.

The upper limit for iron is 45 mg iron/person/day for adults (≥19 years of age) and adolescents (14-18 years), and 40 mg iron/person/day for infants (0-12 months) and children (1-13 years).

The compositions of the invention may be useful in achieving the DRI for iron during the course of a subject's dietary intake.

The compositions of the invention may reduce the effect of iron fortification on the organoleptic properties (e.g. colour or taste) of the food or beverage in comparison to other iron-fortifying compositions. For example, the use of the compositions of the invention may improve the stability of the colour of the food or beverage fortified with iron (e.g. reduce the change in colour of the food or beverage as a result of iron fortification with the compositions of the invention in comparison with other iron compositions, such as ferrous sulfate or ferric pyrophosphate).

Organoleptic properties of foods and beverages may be readily measured by the skilled person. For example, the colour of food may be measured using the CIE 1976 L*a*b* (CIELAB) colour scale proposed by the Commission Internationale de l'Eclairage (CIE; CIE Technical Report, Colorimetry 2nd Edition, CIE 15.2 (1986, corrected reprint 1996)). The CIELAB colour space is produced by plotting the quantities L*, a*, b* in rectangular coordinates. The L* coordinate of an object is the lightness intensity as measured on a scale from 0 (black) to 100 (absolute white). The a* and b* coordinates have no specific numerical limits. The parameter a* runs from pure green (negative a*) to pure red (positive a*), while b* runs from pure blue (negative b*) to pure yellow (positive b*).

In the CIELAB colour space, colour difference may be calculated as a single value taking into account the differences between the L*, a* and b* values of two samples. The colour difference ΔEab* is calculated as follows:

$$\Delta Eab^* = \sqrt{(\Delta L^*)^2 + (\Delta a^*)^2 + (\Delta b)^2}$$

The compositions of the invention may be used to prevent colour change over a food or beverage product's shelf-life. For example, the CIELAB ΔEab* colour difference between an iron-fortified food product at the time of its manufacture and the end of its shelf-life under recommended storage conditions may be less than 3, for example less than 2.

Shelf life is the recommended length of time that foods, beverages and many other perishable items can be stored during which the defined quality of a specified proportion of the goods remains acceptable under expected (or specified) conditions of distribution, storage and display. Typically a "best before date" (BBD) is printed on packaged perishable foods together with recommended storage conditions. Where such a BBD is indicated, the shelf-life is the time between manufacture and the BBD. Where a BBD is not indicated, the shelf-life is the equivalent period usual for the relevant product type.

The compositions of the invention may be used to prevent colour change during heat treatment of a food or beverage product. For example, the iron-fortified food product may have a ΔEab* value less than 3, for example less than 2, after a heat treatment of 2 minutes at 105° C.

Iron

The skilled person will have a detailed and thorough understanding of iron chemistry and biochemistry, and the use of iron in nutritional supplementation. Briefly, Fe(III) ions are iron ions of the +3 oxidation state. They may also be referred to as $Fe^{3+}$ ions or ferric ions. Fe(II) ions are iron ions of the +2 oxidation state. They may also be referred to as $Fe^{2+}$ ions or ferrous ions.

Sources of Fe(III) that may be used to produce the complexes or compositions of the present invention are not particularly limited, provided that they are suitable for ingestion by animals, preferably humans (e.g. are non-toxic). Example sources of Fe(III) include Fe(III) sulfate, Fe(III) citrate, Fe(III) choline citrate, Fe(III) ammonium citrate and Fe(III) chloride. Preferably, the source of Fe(III) is Fe(III) sulfate.

Phytic Acid

Phytic acid is a naturally-occurring compound found, for example, in grains, legumes, seeds and nuts in the form of phytates or phytic acid itself. Phytic acid compounds provide the principal plant storage form of phosphorus.

As used herein, "phytic acid" refers to a myo-inositol phosphate, i.e. myo-inositol monophosphate (InsP), myo-inositol bisphosphate (InsP$_2$), myo-inositol triphosphate (InsP$_3$), myo-inositol tetrakisphosphate (InsP$_4$), myo-inositol pentakisphosphate (InsP$_5$) or myo-inositol hexakisphosphate (InsP$_6$). Preferably, the phytic acid is myo-inositol hexakisphosphate.

myo-Inositol hexakisphosphate has the structure:

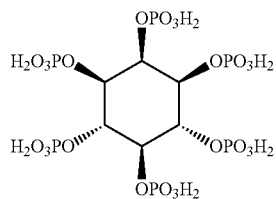

Advantageously, phytic acid may be regarded as a natural ingredient for delivering highly bioavailable iron, because it can be readily obtained from natural sources. For example sources of phytic acid include cereals (e.g. wheat, corn, oat, barley, sorghum, millets, rice and bran), beans (e.g. peas, lentils, white beans and soybeans), tubers (e.g. potato, yam, sweet potato and sugar beet), fruit (e.g. plantain, dates, strawberry and avocado), leafy vegetables (e.g. spinach, red cabbage, okra, cauliflower, carrots and tomato), nuts (e.g. hazelnut, walnut, almond and cashew), and other foods such as coconut, sesame seeds and coriander.

Amino Compound

As used herein, "amino compound" refers to a compound comprising an amine functional group, i.e. a nitrogen atom joined by single bonds to hydrogen atoms, alkyl groups and/or aryl groups. Preferably, the amino compound is a basic compound.

Amino compounds that may be used in the present invention are not particularly limited, provided that they are suitable for ingestion by animals, preferably humans (e.g. are non-toxic).

In one embodiment, the amino compound is selected from the group consisting of ammonium hydroxide; ammonium carbonate; ammonium phosphate dibasic; ammonium sodium phosphate dibasic and triammonium phosphate.

In a preferred embodiment, the amino compound is ammonium hydroxide

Method of Preparation

In one aspect, the present invention provides a method of preparing a water-soluble composition, wherein the method comprises the steps:
(a) mixing in an aqueous solution a source of Fe(III), phytic acid, an amino compound and optionally an amino acid; and
(b) optionally heating the mixture, preferably to at least 50° C., wherein the amino compound is selected from the group consisting of ammonium hydroxide; ammonium carbonate; ammonium phosphate dibasic; ammonium sodium phosphate dibasic and triammonium phosphate.

The present invention also provides a method of preparing a water-soluble composition, wherein the method comprises the steps:
(a) mixing in an aqueous solution a source of Fe(III), phytic acid, an amino compound and optionally an amino acid; and
(b) optionally heating the mixture, wherein the composition does not comprise a carboxylic acid-containing compound other than an optional amino acid.

Following combination of all the components in step (a), it may be necessary to continue mixing until the composition dissolves. For example, it may be necessary to continue mixing for at least 6, 12, 18, 24, 30, 36, 42 or 48 hours. The time taken for the composition to dissolve may be reduced by heating the mixture, for example to at least 50° C., 60° C., 70° C. or 80° C.

By way of example, the method may comprise adding the source of Fe(III) (e.g. Fe(III) sulfate) to an aqueous phytic acid solution with stirring. Typically, the Fe(III) phytate will precipitate within a short timeframe. The amino compound and optionally amino acid may then be added to the solution in amounts necessary to provide the desired ratio of components. The composition may then be stirred until the components have dissolved.

Food and Beverage Products

The compositions of the invention are suitable for fortifying food and/or beverages products. In addition, the invention also encompasses food or beverage products which have been fortified with the compositions of the present invention.

A wide range of food or beverage products may be fortified with iron using the compositions of the invention and a range of non-limiting examples are described below.

The food or beverage products may, for example, be products selected from yoghurt, bouillon, water (e.g. bottled water), seasoning, sauce, milk powder, milk drink, milk-based dessert, pet food, cereal, pasta, noodle or baby food products.

Beverages are liquids consumed for refreshment or nourishment and include alcoholic and non-alcoholic drinks, carbonated drinks, fruit or vegetable juices and hot drinks, such as coffee or tea.

The compositions, or food or beverage products of the present invention may contain (e.g. may have been supplemented with) additional vitamins, minerals and micronutrients, including trace elements, in accordance with the recommendations (e.g. recommended daily intake guidelines) of government bodies.

Fruit Products

The food or beverage products may comprise fruit or a component thereof. For example, the products may comprise fruit juice such as, but not limited to juice derived from an orange, apple, mango, peach, banana, date, apricot, grape fruit, papaya, pineapple, raspberry, strawberry, pear, tangerine and/or cherry.

The food or beverage products may, for example be fruit juice or may be in the form of a fruit puree which comprises fruit juice among other fruit components.

The food or beverage products may comprise fruit or a component thereof.

The problem of colour change when fortifying food with iron is particularly apparent with food compositions containing fruit. The colour of many fruits is derived from phenolic chromophore compounds and so addition of iron leads to a bathochromic shift in the colour of the phenolic chromophore compounds resulting in an undesirable change in the colour of the food.

Fruits are the fleshy seed-associated structure of a plant that are sweet and edible in the raw state, such as apples, oranges, grapes, strawberries and bananas. Fruits are often eaten as desserts in European cultures. The term fruit in the current specification includes seedless fruits such as seedless grapes and common varieties of bananas.

The fruit may, for example, be selected from the group consisting of blackcurrant, cranberry, elderberry, red currant, boysenberry, grape, cherry, orange, lemon, lime, mandarin, tangerine, grapefruit, pineapple, mango, papaya, passion fruit, kiwifruit, guava, fig, date, apple, plum, strawberry, raspberry, blueberry, blackberry, apricot, pear, banana, quince, wolfberry and mixtures of these.

The fruit may, for example, be in the form of fresh fruit, fresh fruit pieces, fruit powder, dried fruit or fruit puree.

Fruit intrinsically provides a good source of beneficial dietary nutrients, and so is a good basis for delivering additional nutritional benefits to food. There is therefore a need to provide iron-fortified food compositions containing fruit which do not exhibit undesirable colour changes.

Yoghurt

The food or beverage products of the invention may be yoghurts or comprise yoghurts.

In the context of the present invention, the term "yoghurt" refers to a non-beverage food produced from the acidification of milk. Acidification is achieved through the addition of an acid, such as lemon juice or vinegar; through bacterial fermentation; or by a combination of acid addition and bacterial fermentation. The term "yoghurt" may include, but is not limited to, materials complying with local food labelling regulations concerning the term "yoghurt".

Yoghurt is a good source of calcium, helping to form and maintain strong bones. Yoghurt may also be fortified with other beneficial minerals such as magnesium and zinc. However, fortifying yoghurt with iron presents a problem if the yoghurt contains phenolic chromophore compounds, such as may be found in yoghurts containing fruit.

For example, a blueberry yoghurt, coloured by the anthocyanins in blueberries, will change colour after addition of iron; the anthocyanins undergoing a bathochromic shift. Similarly a banana yoghurt, which was initially a pale yellow colour, may develop an unattractive grey-blue colour on addition of iron. Bananas comprise polyphenols such as gallic acid, catechin, epicatechin and epigallocatechin.

The present invention provides iron-fortified food or beverage products comprising yoghurt where these colour change problems do not occur.

Bouillon

The food or beverage products of the invention may be bouillons.

Bouillons, also referred to as broths, are commonly used as flavourings during cooking. They may be prepared by heating (e.g. simmering) ingredients such as meat and/or bones (e.g. from beef or poultry), vegetables and/or herbs in water. Bouillons are regarded as particularly difficult to fortify with iron without affecting their organoleptic properties.

The bouillons may be in the form of dehydrated bouillons, for example bouillon cubes or granular bouillon. Such products are commonly used to add flavour during cooking.

Other Products

The food or beverage products of the invention may be biscuit, cake or pastry products; a cereal bar; cereal, such as a breakfast cereal; an ice cream product; a dessert; a prepared meal; a nutritional supplement or a pet food product.

All of these products may pose problems of colour change when fortified by iron. For example biscuit, cake and pastry products may be coloured by natural colours such as anthocyanins or carmine; the products may have coloured fillings or coatings. Breakfast cereals may contain fruit, for example fruit inclusions or fruit fillings. Cereal bars may contain coloured fruit such as cranberries, or have coloured inclusions containing added vitamins and minerals, such as small chewy pieces of jelly. Ice creams and desserts may be coloured by anthocyanins, particularly when fruit flavoured. Prepared meals and nutritional supplements may contain fruits or vegetables for example in the form of vegetable powder, or may be coloured by the addition of natural colours to make them more appealing. Pet foods such as dog treats may contain fruit, for example berries. All these products may be sensitive to colour change on addition of iron, which may be reduced or eliminated by using the compositions of the invention.

Therapeutic Nutritional Composition

The food or beverage products of the invention may be in the form of a therapeutic nutritional composition. The composition may be a nutritionally complete formula, for example including a source of protein, carbohydrate and fat.

EXAMPLES

Materials and Methods

Dodecasodium phytate was obtained from A & Z Food Additives CO., LTD (China); 50% phytic acid solution was obtained from Tsuno Rice Inc.; 80% ferric sulfate was obtained from Dr. P. Lohmann GmbH KG; lysine monohydrate was obtained from Evonik Industries AG; arginine and histidine were obtained from Kyowa Hakko Europe GmbH; 37% HCl was obtained from Merck; and 26% ammonium hydroxide and glycine were obtained from Sigma Aldrich.

Phytic Acid Solution

In a typical preparation, dodecasodium phytate (18 g, 19.5 mmol) was dissolved in 300 g of MilliQ water and 37% HCl (11.6 g, 0.11 mol) to give a final pH of 1.6 units and a concentration of 3.9% by weight of phytic acid.

Ferric Sulfate

80% pure ferric sulfate (3.34 g, 8 mmol) was dissolved in a 500 mL glass bottle in 100 g of MilliQ water to give a concentration of 5% by weight of ferric sulfate.

Amino Acid Solutions

Amino acids were dissolved in 500 mL glass bottles as described in Table 1.

TABLE 1

| Amino acid | Supplier | Amount (g) | Amount (mmol) | Water amount (g) | Concentration (% weight) |
|---|---|---|---|---|---|
| Lysine monohydrate (MW 164.2) | Evonik | 64.3 | 400 | 100 | 40% |
| Arginine (MW 174.2) | Kyowa Hakko Europe GmbH | 75.1 | 430 | 500 | 13% |
| Histidine (MW 155.15) | Kyowa Hakko Europe GmbH | 75.8 | 488 | 2000 | 3.65% |

Ammonium Hydroxide Solution

26% ammonium hydroxide (500 mL) was diluted with 500 mL of MilliQ water in a 1 L glass bottle to give a concentration of 13% by weight.

TABLE 2

| Exp. No. | Phytic acid (PA) solution | | | | Ferric sulfate solution | | | Amino acid (AA) solution | | | | Ammonium hydroxide solution | | Complex |
| --- | --- | --- | --- | --- | --- | --- | --- | --- | --- | --- | --- | --- | --- | --- |
| | Conc. (%) | Amount (g) | Amount (mmol) | Ratio to PA | Conc. (%) | Amount (g) | Amount $Fe^{3+}$ (mmol) | AA | Ratio to PA | Amount (g) | Amount (mmol) | Ratio to PA | Amount (g) | Conc. (%) |
| 1 | 4.0 | 45 | 2.75 | 0.5 | 2.6 | 10 | 1.3 | — | — | — | — | 2.3 | 1.7 | 4.0 |
| 2 | 4.0 | 45 | 2.75 | 0.5 | 2.6 | 10 | 1.3 | Arg | 4.2 | 15.5 | 11.5 | — | — | 5.8 |
| 3 | 4.0 | 45 | 2.75 | 0.5 | 2.6 | 10 | 1.3 | Lys | 5 | 5 | 13.5 | — | — | 6.8 |
| 4 | 4.0 | 45 | 2.75 | 0.5 | 2.6 | 10 | 1.3 | His | 14.2 | 150.5 | 39 | — | — | 3.7 |
| 5 | 3.9 | 67.2 | 4 | 1 | 5.2 | 15 | 3.9 | — | — | — | — | 7.4 | 7.9 | 4.9 |
| 6 | 3.9 | 67.2 | 4 | 1 | 5.2 | 15 | 3.9 | Arg | 12 | 64 | 47 | — | — | 8.0 |
| 7 | 3.9 | 67.2 | 4 | 1 | 5.2 | 15 | 3.9 | Arg | 6 | 32 | 23.5 | 4 | 4.15 | 6.8 |
| 8 | 3.9 | 67.2 | 4 | 1 | 5.2 | 15 | 3.9 | Lys | 12 | 20 | 48 | — | — | 11.2 |
| 9 | 3.9 | 160 | 9.4 | 1 | 5 | 37.5 | 9.4 | His | 1 | 40 | 9.4 | 3.5 | 9 | 4.4 |
| 10 | 3.9 | 160 | 9.4 | 1 | 5 | 37.5 | 9.4 | His | 2 | 80 | 18.8 | 3.5 | 9 | 3.9 |
| 11 | 3.9 | 160 | 9.4 | 1 | 5 | 37.5 | 9.4 | His | 4 | 160 | 37.6 | 3.4 | 8.5 | 4.1 |
| 12 | 3.9 | 160 | 9.4 | 0.75 | 5 | 28.0 | 7.05 | — | — | — | — | 3.3 | 8.1 | 4.0 |

TABLE 3

| Exp. No. | Phytic acid (PA) | | | | Iron | | | Amino acid | | | | Ammonium hydroxide | |
| --- | --- | --- | --- | --- | --- | --- | --- | --- | --- | --- | --- | --- | --- |
| | [PA] | Amount (g) | Amount (mmol) | Ratio to PA | [Ferric sulfate] | Solution amount (g) | Amount $Fe^{3+}$ (mmol) | Type | Molar ratio to PA | Solution amount (g) | Amount (mmol) | Molar ratio to PA | Solution amount (g) |
| 13 | 3.9% | 160 g | 9.4 | 1 | 5% | 37.5 g | 9.4 | Histidine | 0.5 | 20 g | 4.7 | 3.5 | 9 g |
| 14 | 3.9% | 160 g | 9.4 | 1 | 5% | 37.5 g | 9.4 | Histidine | 1 | 40 g | 9.4 | 3.5 | 9 g |
| 15 | 3.9% | 160 g | 9.4 | 1 | 5% | 37.5 g | 9.4 | Histidine | 2 | 80 g | 18.8 | 3.5 | 9 g |
| 16 | 3.9% | 160 g | 9.4 | 1 | 5% | 37.5 g | 9.4 | Histidine | 4 | 160 g | 37.6 | 3.4 | 8.5 g |

Example 1—Fe:Phytic Acid:Amino Acid Complex

The ferric sulfate solution was added drop-wise to the phytic acid solution at pH 1.6 in a 500 mL glass bottle. The solution became turbid and a white precipitate was observed after a few seconds of the addition. The amino acid and/or ammonium hydroxide solutions were then added to this milky solution using the amounts reported in Table 2 until a final pH of 7±1 was reached. After stirring for between 24-48 h, the solution became clear and the product was freeze dried to provide a light yellow/white powder.

Example 2—Fe:Phytic Acid:Amino Acid Complex with Heating

The ferric sulfate solution was added drop-wise to the phytic acid solution at pH 1.6 in a 500 mL glass bottle. The solution became turbid and a white precipitate was observed after a few seconds of the addition. The amino acid and/or ammonium hydroxide solutions were then added to this milky solution using the amounts reported in Table 3 until final pH of 7±1 was reached.

The bottle was then placed in a water bath at different temperatures of 60, 70 and 80° C. to accelerate the dissolution. The results are shown in Table 4.

The level of iron in Exp 13 was too high to be soluble with a molar ratio of amino acid to phytic acid of 0.5, but at a lower relative quantity of iron this molar ratio of amino acid to phytic acid is soluble (see Exp 20 in Example 8).

TABLE 4

| | Dissolution time v. temperature | | | |
| --- | --- | --- | --- | --- |
| Exp. No. | Ambient temperature at 24 h | A 60° C. | B 70° C. | C 80° C. |
| 13 | Not Soluble | Not Soluble | Not Soluble | Not Soluble |
| 14 | Not Soluble | 8 hours | 8 hours | N.A. |
| 15 | Not Soluble | 4 hours | 4 hours | 3 hours |
| 16 | Not Soluble | 2 hours | 2 hours | 1 hour |

Example 3—Fe:Phytic Acid:Amino Acid Complex with Different Fe Ratios

80% pure ferric sulfate was solubilised in 50 mL of MilliQ water in a 500 mL glass bottle (in the varying amounts shown in Table 5) and added drop-wise to a 4.5% solution of phytic acid at pH 2.1 (100 mL, 6.8 mmol).

Histidine (8.42 g, 54 mmol) was then added drop-wise in combination with 13% ammonium hydroxide (20-30 mL) until a final pH of 7-7.5 was reached. The solution was stirred for 24-48 hours. The results are shown in Table 5.

TABLE 5

| | Exp. No. | | | |
| --- | --- | --- | --- | --- |
| | 17 | 18 | 19 | 20 |
| Fe:phytic acid ratio | 1.2 | 1.6 | 2.0 | 2.4 |
| Amount ferric | 2 | 2.7 | 3.4 | 4 |

TABLE 5-continued

| | Exp. No. | | | |
|---|---|---|---|---|
| | 17 | 18 | 19 | 20 |
| sulfate (g/50 mL MilliQ water) | | | | |
| Amount $Fe^{3+}$ (mmol) | 8 | 11 | 13.5 | 16 |
| Final Fe content (%) | 2.3 | 3.1 | 3.9 | 4.6 |
| Results after 24-48 h at room temperature | Soluble | Soluble | Partially Soluble | Partially Soluble |

Example 4—Increase of Percent Total Solid Content in the Complex Preparation In a 200 mL glass bottle, ferric sulfate (9.4 g) was added to the phytic acid solution under mechanical stirring. The solution became turbid and a white precipitate was observed after a few seconds. The amino acid was then added to the slurry and the solution was stirred for an additional 2 h at room temperature. After this period, a 26% ammonium hydroxide solution was added until a final pH of 7-8 was reached. The suspension was stirred at room temperature for 24-48 h until clear.

| Phytic acid source | Amount used | Amino acid | Final % total solid |
|---|---|---|---|
| Phytic acid 50% weight | 50 g | Lysine 5.5 g | 61.5 |
| | | Arginine 6.6 g | 62.1 |
| | | Glycine 2.8 g | 59.9 |
| Sodium Phytate 35% in 1M HCl | 100 g | Lysine 5.5 g | 28.2 |
| | | Arginine 6.6 g | 28.9 |
| | | Glycine 2.8 g | 26.5 |

Example 5—Colour Change in Iron-Fortified Strawberry and Banana Yoghurt

Commercial Nestle Jogolino™ Strawberry/Banana yoghurt containing 15% banana puree and 10% strawberry puree was iron fortified by the addition of different iron ingredients as reported in Table 6. The amounts were chosen to provide approximately 0.8 mg of iron per 100 g yoghurt. In parallel, the yoghurt was also fortified with soluble Fe complexes described above. Each iron ingredient was added to the yoghurt and stirred under argon for 20 minutes. A further sample without iron fortification was also prepared in the same manner. All samples were heat treated at 105° C. for 2 minutes and colour measurements were carried out after the samples returned to room temperature.

TABLE 6

Preparation of fortified Jogolino

| Trial | Fe ingredient | % Fe | Amount used (mg)/140 g yoghurt |
|---|---|---|---|
| Blank | — | — | — |
| A | Ferric pyrophosphate | 21 | 5.3 |
| B | Exp. No. 2 | 1.36 | 82.4 |
| C | Exp. No. 3 | 1.43 | 78.3 |
| D | Exp. No. 4 | 0.72 | 155.6 |
| E | Exp. No. 10 | 3.29 | 34.0 |
| F | Exp. No. 11 | 2.70 | 41.5 |

Colour measurements were performed in 1×1 cm polystyrene cuvettes using an XRite ColorEye 7000A colorimeter. The colorimeter was set up with a D65 light source, 10 degree observer angle and specular component included. The colour difference between the beverage with no iron and with the iron fortified beverages was measured and expressed as ΔEab* using the CIELAB colour scale (Table 7).

TABLE 7

Results on Jogolino colour stability

| Trial | Fe ingredient | ΔEab* |
|---|---|---|
| A | Ferric pyrophosphate | 1.91 |
| B | Exp. No. 2 | 1.28 |
| C | Exp. No. 3 | 1.62 |
| D | Exp. No. 4 | 1.56 |
| E | Exp. No. 10 | 2.48 |
| F | Exp. No. 11 | 1.27 |

Example 6—Colour Change in Iron-Fortified Maggi Chicken Bouillon

Commercial Maggi Chicken Bouillon containing curcumin was iron fortified by the addition of different iron ingredients as reported in Table 8. The amounts were chosen to provide approximately 5.5 mg of iron per 6.55 g of bouillon powder. In parallel, the bouillon was also fortified with soluble Fe complexes described above. A further sample without iron fortification was also prepared in the same manner. All samples were reconstituted in 250 mL of boiling water and kept at 60° C. for a minimum of 30 minutes.

TABLE 8

Preparation of fortified bouillon cube

| Trial | Fe ingredient | % Fe | Amount used (mg)/6.55 g bouillon |
|---|---|---|---|
| Blank | — | — | — |
| A | Ferrous sulfate | 20.0 | 27.5 |
| B | Ferric pyrophosphate | 21.0 | 26.2 |
| C | Exp. No. 2 | 1.36 | 404.5 |
| D | Exp. No. 3 | 1.43 | 384.75 |
| E | Exp. No. 4 | 0.72 | 764.2 |
| F | Exp. No. 10 | 3.29 | 167.2 |
| G | Exp. No. 11 | 2.70 | 203.8 |
| H | Exp. No. 12 | 2.00 | 271.0 |
| I | Exp. No. 14B | 0.91 | 603.3 |
| J | Exp. No. 14C | 0.91 | 603.3 |
| K | Exp. No. 15A | 0.785 | 700.9 |
| L | Exp. No. 15C | 0.785 | 700.9 |
| M | Exp. No. 16C | 0.645 | 854.3 |

Colour measurements were performed in 2.6×1 cm quartz cuvettes using an XRite ColorEye 7000A colorimeter. The colorimeter was set up with a D65 light source, 10 degree observer angle, specular component included and Large area View (LAV). The colour difference between the beverage with no iron salts and the iron-fortified beverages was measured for each ferrous salt and expressed as ΔEab* using the CIELAB colour scale (Table 9).

TABLE 9

Results on Maggi Chicken Bouillon stability

| Trial | Fe ingredient | ΔEab* |
|---|---|---|
| A | Ferrous sulfate | 11.5 |
| B | Ferric pyrophosphate | 6.4 |
| C | Exp. No. 2 | 5.2 |
| D | Exp. No. 3 | 4.4 |
| E | Exp. No. 4 | 3.5 |
| F | Exp. No. 10 | 5.8 |
| G | Exp. No. 11 | 4.5 |
| H | Exp. No. 12 | 6.2 |
| I | Exp. No. 14B | 5.5 |
| J | Exp. No. 14C | 4.1 |
| K | Exp. No. 15A | 4.8 |
| L | Exp. No. 15C | 5.6 |
| M | Exp. No. 16C | 6.3 |

Example 7—Fortification of Water

Processed water enriched with 20-30 ppm of sodium and potassium (600 mL) was iron fortified by the addition of different iron ingredients as reported in Table 10. The amounts were chosen to provide approximately 2.1 mg of iron per litre of water. The water was stored in an oven at 40° C. for 18 weeks. The iron content was measured for each sample through ICP-AES.

TABLE 10

| Trial | Fortificant | Week 1 | Week 18 |
|---|---|---|---|
| A | $FeSO_4 \times H_2O$ | 0 (Precipitate) | 0 (Precipitate) |
| B | Exp. No. 18 | 1.95 | 2.01 |

While ferrous sulfate precipitates almost instantaneously, the soluble iron complex remained in solution for up to 18 weeks without giving any sign of decomposition or precipitation.

Example 8—Fe:Phytic Acid Complexes with Ammonium Hydroxide and Different Amino Acids In a 250 mL glass bottle, a 80% pure ferric sulfate was solubilized in 25 mL of MilliQ water (see table) and added drop wise to a 50% solution of phytic acid at pH 2.1 (12 g, 9 mmol) previously diluted in 15 ml deionized water.

| | Exp | | | |
|---|---|---|---|---|
| | 20 | 21 | 22 | 23 |
| PA:Fe:AA Ratio | 1:0.5:0.5 | 1:1:2 | 1:1:2 | 1:1.7:2.5 |
| Fe Amount in g/25 mL MilliQ | 1.9 | 3.78 | 3.78 | 6.78 |
| Histidine (g) | 1.2 | 2.4 | 2.4 | 1.2 |
| Glycine (g) | | | 1.1 | 2.3 |
| Glutamine (g) | | 4.4 | | |
| Results after heat treatment | Soluble | Soluble | Soluble | Soluble |
| Fe content | 2.1% | 3.5% | 3.6% | 5.9% |

After the amino acids were added (as in the table), the bottles were shaken for 1 h at room temperature under continuous agitation. The pH was adjusted to 5.5 with a 26% solution of ammonium hydroxide. The temperature was raised to 65° C. for 35 minutes.

Example 9—Production of Larger Quantities Spray Dried with Maltodextrin

| | Phytic Acid g | Ferric Sulphate g | Histidine g | Glycine g | Maltodextrin g |
|---|---|---|---|---|---|
| Exp 24 | 1000 | 189 | 117.6 | 113.8 | 400 |

Phytic acid (1000 g) was added into a 5 L reactor and diluted with demineralised water (1 L) and cooled to 0° C. Ferric sulfate was dissolved in cold demineralized water (1 L) and added while being agitated with a peristaltic pump over 1 h. Histidine and Glycine were added and the mixture was stirred for 1 h. The pH was adjusted to pH to 5.5 with 26% $NH_4OH$. After this period the temperature was increased to 15° C. and maltodextrin DE21 was added. The blend was pasteurized at 65° C. for 35 minutes and directly spray dried using common conditions. Fe content was determined through ICP-AES to give an iron content of 2.6%.

Example 10—In-Vitro Bioaccessiblity Tests

Bioaccessiblity tests were conducted on a modified version of the digestion model proposed by Forbes et al. (Comparison of in vitro, animal, and clinical determinations of iron bioavailability: International Nutritional Anemia Consultative Group Task Force report on iron bioavailability, Am J Clin Nutr 1989; 49:225-38.

The samples were kept at pH 1.7 for the initial 6 minutes to simulate stomach digestion and then at pH 7 to simulate the intestine tract.

Iron compounds were weighed as described in the table below.

| Sample name | % Fe | Amount of salt (mg) |
|---|---|---|
| Ferrous Sulphate | 20% | 100 |
| Ferric Pyrophosphate | 21% | 95 |
| Exp 21 | 3.5% | 571 |
| Exp 22 | 3.6% | 769 |
| Exp 23 | 5.9% | 339 |

Each salt was dissolved in 37° C. hot 0.02 M HCl (250 mL) in a 500 mL conical flask and 250 mL. These flask were gently agitated in a water batch at 37° C. 180 min. Samples (2 mL) were taken at 0, 15, 30, 60 and 90 minutes. After this the pH was adjusted to 7 by adding a few drops 13% ammonium hydroxide. Samples were taken at 100 and 120 minutes. All samples were diluted to 15 mL in a test tube with 1 M $HNO_3$. Fe content was measured by Atomic Emission Spectroscopy and relative Bioaccessiblity calculated on the basis of ferrous sulfate ash shown in FIG. 1.

From FIG. 1, $FeSO_4$ is readily soluble at acidic pH but precipitation occurs at neutral pH. FePP is not soluble in either of the two pH levels. Solubility of PA:Fe amino acid complexes is not disturbed by the pH variation. As solubility is a significant factor in bioavailability, this indicates a potential better availability for the PA:Fe amino acid complexes than for $FeSO_4$ and FePP.

All publications mentioned in the above specification are herein incorporated by reference. Various modifications and variations of the described compositions, uses, products and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A composition for fortifying food and/or beverages comprising a complex of Fe(III), phytic acid and an amino compound selected from the group consisting of ammonium hydroxide; ammonium carbonate; ammonium phosphate dibasic; ammonium sodium phosphate dibasic; and triammonium phosphate.

2. The composition of claim 1, wherein the amino compound is ammonium hydroxide.

3. The composition of claim 1 comprising an amino acid.

4. The composition of claim 1, wherein:
(a) the molar ratio of Fe(III) to phytic acid is about 0.1:1 to about 4:1;
(b) the molar ratio of the amino compound to phytic acid is about 0.5:1 to about 20:1; and/or
(c) the molar ratio of the amino acid to phytic acid is about 0.1:1 to about 15:1.

5. The composition of claim 1 which is in the form of an aqueous solution or a water-soluble solid.

6. A method for producing a composition for fortifying food and/or beverages, comprising mixing an Fe(III) compound, phytic acid and an amino compound selected from the group consisting of ammonium hydroxide; ammonium carbonate; ammonium phosphate dibasic; ammonium sodium phosphate dibasic and triammonium phosphate.

7. A method for fortifying food and/or beverages of claim 6, wherein the composition does not comprise a carboxylic acid-containing compound other than an optional amino acid.

8. A composition for fortifying food and/or beverages comprising a complex of Fe(III), phytic acid and an amino compound, wherein the composition does not comprise a carboxylic acid-containing compound other than an optional amino acid.

9. A method for fortifying a food or beverage comprising adding thereto a complex of Fe(III), phytic acid and an amino compound selected from the group consisting of ammonium hydroxide; ammonium carbonate; ammonium phosphate dibasic; ammonium sodium phosphate dibasic; and triammonium phosphate.

* * * * *